United States Patent
Grass et al.

(10) Patent No.: US 10,219,772 B2
(45) Date of Patent: Mar. 5, 2019

(54) TOMOGRAPHIC IMAGING DEVICE AND METHOD FOR SPARSE ANGULAR SAMPLING

(71) Applicant: KONINKLIJKE PHILIPS N.V., Eindhoven (NL)

(72) Inventors: Michael Grass, Buchholz in der Nordheide (DE); Thomas Koehler, Norderstedt (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/547,531

(22) PCT Filed: Dec. 12, 2016

(86) PCT No.: PCT/EP2016/080539
§ 371 (c)(1),
(2) Date: Jul. 31, 2017

(87) PCT Pub. No.: WO2017/102607
PCT Pub. Date: Jun. 22, 2017

(65) Prior Publication Data
US 2018/0289352 A1 Oct. 11, 2018

(30) Foreign Application Priority Data
Dec. 18, 2015 (EP) .................................... 15201228

(51) Int. Cl.
*A61B 5/00* (2006.01)
*A61B 6/00* (2006.01)
(Continued)

(52) U.S. Cl.
CPC ............ *A61B 6/542* (2013.01); *A61B 5/0077* (2013.01); *A61B 6/027* (2013.01); *A61B 6/032* (2013.01);
(Continued)

(58) Field of Classification Search
CPC ......... A61B 6/589; A61B 6/544; A61B 6/542; A61B 5/0077; A61B 6/027; A61B 6/032;
(Continued)

(56) References Cited

U.S. PATENT DOCUMENTS

| | | | | |
|---|---|---|---|---|
| 5,559,846 A * | 9/1996 | Tam | ..................... | G06T 11/006 378/4 |
| 6,411,670 B1 * | 6/2002 | Besson | ................. | G06T 11/005 378/4 |

(Continued)

FOREIGN PATENT DOCUMENTS

WO 2014206794 12/2014

OTHER PUBLICATIONS

Dogandzic, et al., "Mask Iterative Hard Thresholding Algorithms for Sparse Image Reconstruction of Objects with Known Contour", Arxiv.org, Cornell University Library, Dec. 2, 2011.

(Continued)

*Primary Examiner* — Thomas J Hong
*Assistant Examiner* — Helene Bor

(57) ABSTRACT

The invention relates to tomographic imaging device (1). The device (1) comprises a radiation detector (3) for measuring radiation traveling through an object to be imaged, the radiation detector (3) being configured to measure radiation only at a plurality of selected sampling positions on a curved track around an axis (z). A planning unit (12) is configured to determine the selected sampling positions on the basis of an estimated contour (44; 53) of the object (21) in a plane (x-y) substantially perpendicular to the axis (z). Further, the invention relates to a method for operating the device (1). The invention is particularly applicable in computed tomography imaging.

20 Claims, 3 Drawing Sheets

(51) Int. Cl.
  *A61B 6/02* (2006.01)
  *A61B 6/03* (2006.01)
  *G01T 1/29* (2006.01)
  *G06T 11/00* (2006.01)
(52) U.S. Cl.
  CPC ............ *A61B 6/4417* (2013.01); *A61B 6/488* (2013.01); *A61B 6/5205* (2013.01); *A61B 6/545* (2013.01); *G01T 1/2985* (2013.01); *G06T 11/003* (2013.01)
(58) Field of Classification Search
  CPC ..... A61B 6/4417; A61B 6/488; A61B 6/5205; A61B 6/545; G01T 1/2985; G06T 11/003
  See application file for complete search history.

(56) References Cited

U.S. PATENT DOCUMENTS

| | | | |
|---|---|---|---|
| 6,901,129 B2* | 5/2005 | Tachizaki | A61B 6/032 |
| | | | 378/4 |
| 7,233,644 B1 | 6/2007 | Bendahan | |
| 7,826,587 B1 | 11/2010 | Langan | |
| 9,486,173 B2* | 11/2016 | Fan | A61B 6/037 |
| 2004/0228439 A1 | 11/2004 | Tsujii | |
| 2007/0073195 A1* | 3/2007 | Chen | A61B 5/1075 |
| | | | 600/594 |
| 2007/0206725 A1* | 9/2007 | Vogtmeier | A61B 6/00 |
| | | | 378/95 |
| 2007/0269093 A1 | 11/2007 | Jones | |
| 2009/0135993 A1* | 5/2009 | Harer | A61B 6/032 |
| | | | 378/4 |
| 2012/0195403 A1 | 8/2012 | Vedantham | |
| 2012/0219116 A1* | 8/2012 | Thompson | G01N 23/04 |
| | | | 378/62 |
| 2014/0233694 A1* | 8/2014 | Wang | A61B 6/583 |
| | | | 378/5 |
| 2015/0327831 A1* | 11/2015 | Levin | A61B 5/0037 |
| | | | 600/427 |
| 2017/0124732 A1* | 5/2017 | Proksa | A61B 6/032 |

OTHER PUBLICATIONS

Kudo, et al., "Image reconstruction for sparse-view CT and interior CT—introductions to compressed sensing and differentiated backprojection", Quant. Imaging Med. Surg., vol. 3, Jan. 1, 2013, pp. 147-161.
Kaganovsky, et al., "Compressed sampling strategies for tomography", Journal of the Optical Society of America A, vol. 31, No. 7, Jul. 1, 2014.
Chen, et al., "Prior image constrained compressed sensing (PICCS): A method to accurately reconstruct dynamic CT images from highly undersampled projection data sets", Medical Physics, AIP, vol. 35, No. 2, Jan. 28, 2008.

\* cited by examiner

TOMOGRAPHIC IMAGING DEVICE AND METHOD FOR SPARSE ANGULAR SAMPLING

CROSS REFERENCE TO RELATED APPLICATIONS

This application is the U.S. National Phase application under 35 U.S.C. § 371 of International Application No. PCT/EP2016/080539 filed Dec. 12, 2016, published as WO 2017/102607 on Jun. 22, 2017, which claims the benefit of European Patent Application Number 15201228.2 filed Dec. 18, 2015. These applications are hereby incorporated by reference herein.

FIELD OF THE INVENTION

The invention generally relates to tomographic imaging. More specifically, the invention is related to a tomographic imaging device, a method for operating a tomographic imaging device and a computer program for carrying out the method. In particular, the invention relates to the sparse angular sampling technique.

BACKGROUND OF THE INVENTION

Popular tomographic imaging techniques include x-ray computed tomography (CT). Particularly in view of potentially harmful effects of CT scans, a recent trend in CT research is the development of imaging techniques which allow for reducing the radiation dose applied to the imaged object, e.g. the body of a patient or part thereof. One related approach involves the reduction of the numbers of projections measured during a CT scan. This can be achieved using the so-called sparse angular sampling technique. In accordance with this technique, projections are acquired only at a number of angular sampling positions, which is selected as small as possible. Hereby, the radiation dose applied to the object can be reduced. Moreover, the acquisition time for acquiring the image can be reduced so that sparse angular sampling can also be advantageously applied in other tomographic imaging techniques, where the sparse angular sampling technique does not result in a reduction of the radiation dose applied to the object, such as Magnetic Resonance Imaging (MRI) and Single-Photon Emission Computed Tomography (SPECT).

In sparse angular sampling, the angular sampling positions are usually selected such that neighboring angular sampling positions have a constant angular distance. Such a selection is optimal in case the object contour is approximately rotation-symmetric with respect to the axis (z-axis) of the tomographic scanner. However, in case of on an asymmetric object contour and/or in case the object is positioned off-center in the examination region of the tomographic scanner, a constant angular distance between the sampling positions leads to an undesired variation of the sampling density (i.e. the number of measured radiation rays through a volume element which correspond to the number of projection lines through a volume element in x-ray CT) within the object. This is due to the fact that the sampling density decreases with an increasing distance from the z-axis. As result, the sampling density in outer object regions having a larger distance to the z-axis (e.g. regions where the object has a larger radial extension) is smaller than the sampling density in outer object regions which have a smaller distance to the z-axis (e.g. region where the object has a smaller radial extension).

Such a variation of the sampling density may lead to an over-sampling of object regions with a higher sampling density (i.e. regions having a smaller distance to the z-axis) or an under-sampling of object regions with a lower sampling density (i.e. regions which have a larger distance to the z-axis), where an over-sampling contravenes the aim of the sparse angular sampling technique and where an under-sampling leads to undesired artifacts in the tomographic images.

A. Dogandzic et. al disclose, in "Mask Iterative Hard Thresholding Algorithms for Sparse Image Reconstruction of Objects with Known Contour", arXiv.org, Cornell University Library, 2 Dec. 2011, that by exploiting both the geometric contour information of the underlying image and sparsity of its wavelet coefficients, a CT image can be reconstructed with a reduced number of measurements.

H. Kudo et. al, reviews, in "Image reconstruction for sparse-view CT and interior CT—introduction to compressed sensing and differentiated backprojection", Quant. Imaging Med. Surg., vol. 3, 1 Jan. 2013, pages 147-161, mathematical principles of the compressed sensing image reconstruction and the differentiated backprojection image reconstruction for sparse-view CT.

SUMMARY OF THE INVENTION

It is therefore, an object of the invention to avoid an over-sampling of object regions with a higher sampling density and an under-sampling of object regions with a lower sampling density, when a tomographic scan is performed using the sparse angular sampling technique.

In a first aspect, the invention suggests a tomographic imaging device, comprising: (i) a radiation detector for measuring radiation traveling through an object to be imaged, the radiation detector being configured to measure radiation travelling along at least one ray path only at a plurality of selected sampling positions on a curved track around an axis; and (ii) a planning unit configured to determine the selected sampling positions on the basis of an estimated contour of the object in a plane substantially perpendicular to the axis.

By determining the selected sampling positions on the basis of the estimated contour of the object, it is possible to determine the selected sampling positions such that an approximately constant sampling density is achieved in the outer regions of the object. Hereby, an over-sampling of object regions with a higher sampling density and an under-sampling of object regions with a lower sampling density can be avoided.

Further, the planning unit is configured to determine the selected sampling positions in such a way that straight paths between intersection points of the same at least one ray path at neighboring selected sampling positions and the contour of the object have an approximately equal length. This allows for a good approximation of the object contour and further reduces the computational complexity of the determination of the selected sampling positions.

In several embodiments, the radiation detector may be movable along the curved track around the axis and/or the radiation detector may occupy a certain portion of the curved track in order to measure radiation at the selected sampling positions. In particular, the curved track may be a circle or spiral. In this case, the axis may correspond to an axis of rotation through the center of the circle or spiral. However, the curved track may also deviate from a circular or spiral shape and may, for example, have an elliptical or another non-circular shape. In this case, the axis may correspond to a suitable axis which is surrounded by the curved track. In particular, it may correspond to an axis which is substantially perpendicular to a tangential and a radial direction with respect to at least one position on the curved track.

In one embodiment, the tomographic imaging device further comprises a radiation source for emitting the radiation, the radiation source and the radiation detector being movable around the object, and the tomographic imaging device comprises a control unit configured to control the radiation source to emit radiation only when the radiation detector is positioned at the selected sampling positions. In particular, the tomographic imaging device may be configured as an x-ray computed tomography device in this embodiment. Therefore, a related embodiment provides that the radiation comprises x-ray radiation and that the radiation detector acquires projection values of the object. When being moved around the object, the radiation source and the radiation detector may particularly be rotated around the aforementioned axis, which may form the axis of rotation in this case.

In one embodiment of the invention, the radiation detector measures radiation traveling along at least one ray path, and the planning unit is configured to determine the selected sampling positions in such a way that paths along the contour of the object between intersection points of ray paths at neighboring selected sampling positions and the contour of the object have approximately equal lengths. Hereby, an approximately constant sampling density can be achieved in the outer regions of the object to be imaged.

With respect to the ray paths, the radiation beam registered by the radiation detector may particularly have a fan or cone shape. In this case, the relevant ray paths used for determining the selected sampling positions correspond to one part of the radiation beam at each selected sampling position. In one implementation, the relevant ray paths may correspond to the central ray paths. In case the tomographic imaging device is configured as an x-ray CT device, the ray paths may correspond to specific projection lines through the object. In the context of this application, when ray path positions are discussed with respect to each other, alternate positions of the same ray path within the radiation beam are meant. The ray paths are preferably central ray paths, but may also be any other ray path in the radiation beam.

In order to determine the selected sampling positions in accordance with the aforementioned embodiment, one related embodiment includes that the planning unit divides the contour of the object into sections of equal length, which correspond to the aforementioned paths along the object contour, and determines the selected sampling positions on the basis of the sections. In further related embodiments, the aforementioned paths along the object contour are approximated by straight lines in order to reduce the computational complexity of the determination of the selected sampling positions.

In one of these embodiments, the planning unit is configured to determine a bisecting line between the ray paths at neighboring selected sampling positions and to determine a straight connection path between said ray paths, which crosses the bisecting line and is substantially perpendicular to the bisecting line, and the planning unit is configured to determine the selected sampling positions in a such a way that the connection paths for neighboring selected sampling positions have a substantially equal length.

In a related embodiment, the connection path is selected such that it crosses an intersection point between the bisecting line and the contour of the object. By determining the straight path between the relevant ray paths of neighboring selected sampling positions in such a way, a good approximation of the object contour can be achieved in many cases.

In a further related embodiment, the connection path is selected such that it crosses the bisecting line between a first and a second point, each of the first and second points corresponding to an intersection point between the bisecting line and a straight line which is substantially perpendicular to the bisecting line and crosses one of the ray paths at the intersection point between the projection line and the contour of the object. In particular, the connection path may be selected such that it crosses the bisecting line at substantially half the distance between said first and second point. In this manner, it also possible to achieve a good approximation of the object contour.

Further, one embodiment of the invention includes that the tomographic imaging device is configured to perform a CT scan to generate a three-dimensional image of the object on the basis of projection values acquired by the radiation detector during the scan, and that the planning unit is configured to estimate the contour of the object on the basis of the image. On the basis of such a three-dimensional image, the object contour can be accurately determined. The CT scan may be a so-called scout CT scan executed with a low x-ray radiation intensity in order to avoid the application of a high radiation dose to the object. Such scout CT scans are often already included in CT examination routines in order to plan the actual CT scan, e.g. to select the slices to be imaged in the actual CT scan. Thus, it is often not necessary to perform an additional scan for determining the sampling positions. Moreover, it is also possible to determine the object contour on the basis of an earlier CT scan of the object, which may also be made using another tomographic imaging device.

In one embodiment, the planning unit is configured to estimate the contour of the object on the basis of at least one two-dimensional image. In a related embodiment, the planning unit is configured to estimate the contour of the object on the basis of two two-dimensional images of the object captured along substantially perpendicular directions. Using one or two two-dimensional images, the planning unit may particularly estimate the contour of the object on the basis of an estimated shape of the object, i.e. on the basis of a model of the object shape.

The one or two two-dimensional image(s) may be generated using the radiation source and the radiation detector of the tomographic imaging device (particularly in case the device is configured as an x-ray CT device). In this embodiment, the image(s) is/are preferably also acquired using a reduced radiation dose. As an alternative, the one or two two-dimensional image(s) may be acquired in a visible spectrum and the device may further comprise a camera for capturing the image(s). It is an advantage of this alternative that the object is not exposed to any hard radiation, such as x-ray radiation, in order to acquire the image(s) and to estimate the object contour.

In a further aspect, the invention suggests a method for operating a tomographic imaging device comprising a radiation detector for measuring radiation traveling through an object to be imaged at sampling positions on a curved track around an axis. The method comprises:

determining selected sampling positions on the basis of an estimated contour of the object in a plane substantially perpendicular to the axis, and controlling the tomographic imaging device such that the radiation detector measures radiation only at the selected sampling positions.

In a further aspect, the invention suggests a computer program executable in a processing unit of a tomographic imaging device, the computer program comprising program code means for causing the processing unit to carry out the aforementioned method.

It shall be understood that the tomographic imaging device of claim 1, the method of claim 14 and the computer program of claim 15 have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
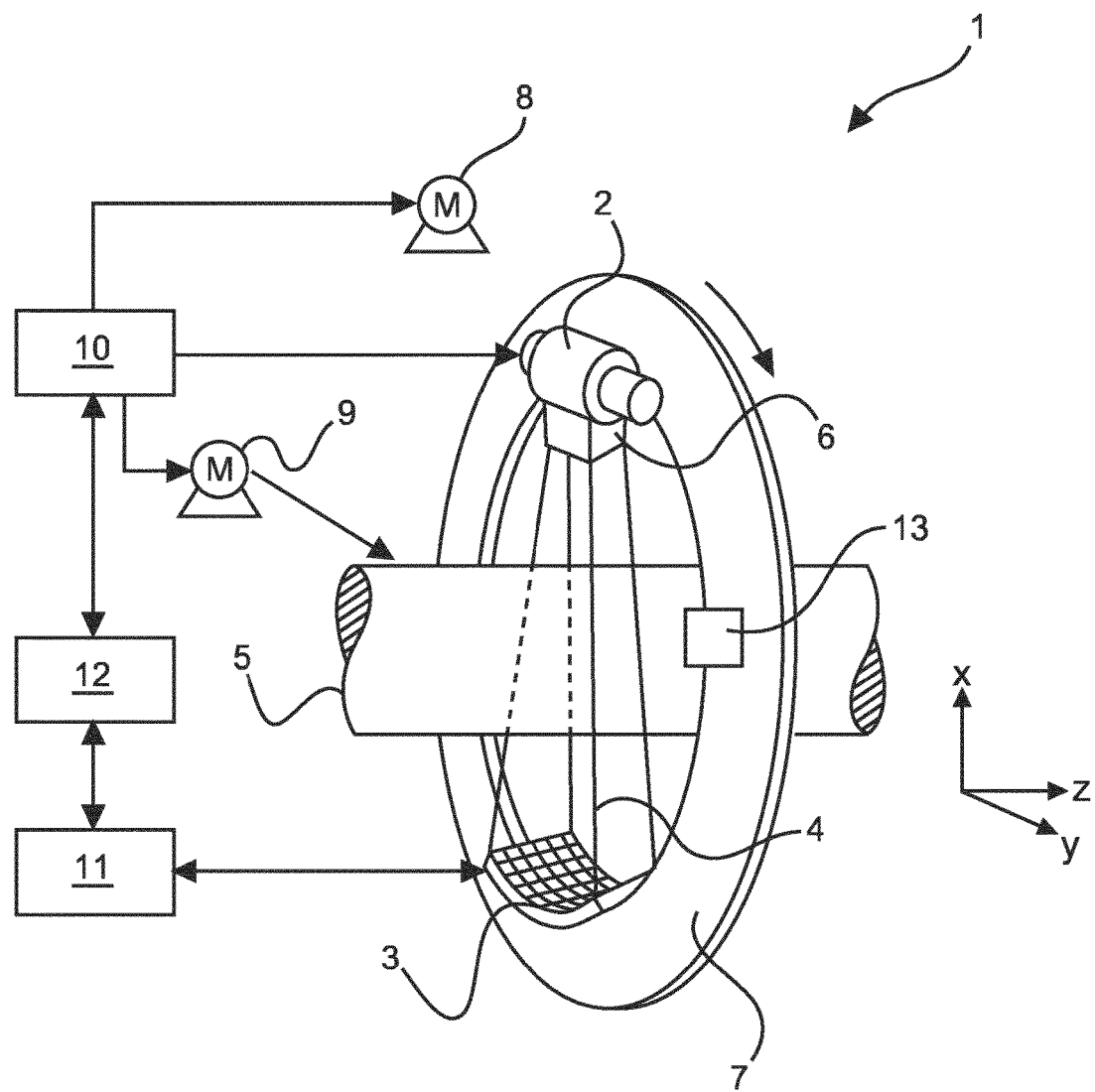
FIG. 1 schematically and exemplarily shows components of an X-ray apparatus according to the invention, FIG. 2 schematically and exemplarily shows sampling positions used for acquiring an image of a rotation-symmetric object, FIG. 3 schematically and exemplarily shows central ray paths of sampling positions used for acquiring an image of a rotation-asymmetric object, FIG. 4 schematically and exemplarily illustrates one procedure for determining the sampling positions for a sparse angular sampling, and FIG. 5 schematically and exemplarily illustrates a further procedure for determining the sampling positions for a sparse angular sampling.

FIG. 1 schematically and exemplarily illustrates components of a tomographic imaging apparatus 1 for imaging an object. In one embodiment, which will also be referred to herein below, the object is a patient body or a part of the patient body. However, the tomographic imaging apparatus 1 may likewise be used to image other objects. Further, the tomographic imaging apparatus 1 may particularly be configured as an x-ray CT apparatus. This will also be assumed in the following description of exemplary embodiments. However, it will be understood by a person skilled in the art that these embodiments may also be applied in the same manner to so-called C-arm CT devices, tomosynthesis devices and similar devices. Moreover, it is possible to use similar methods in connection with other tomographic imaging devices, such as MRI devices and SPECT devices.

The exemplary CT apparatus 1 of FIG. 1 comprises an x-ray source 2, such as an x-ray tube, and a radiation detector 3. More specifically, the x-ray source 2 is configured as a switched source, particularly as a so-called grid-switched x-ray tube, which can be turned on an off in short time intervals. When switched on, the x-ray source 2 emits an x-ray beam 4 which traverses an examination region 5 between the x-ray source 2 and the radiation detector 3 before x-ray radiation is collected by the radiation detector 3. The x-ray beam 4 may be a fan or cone beam or may be configured in another way, such as, for example as a parallel beam. For shaping the x-ray beam, the x-ray source 2 may be provided with a suitable collimator 6. The radiation detector 3 comprises a preferably two dimensional array of detector elements, which are usually also referred to as pixels, where the array may be flat or curved. Within each pixel, incident x-ray radiation produces an electric signal in accordance with the radiation intensity. This signal is read by read out electronics of the radiation detector 3 (not shown in the figure), which provides the signal to a reconstruction unit 11 for generating images.

The x-ray source 2 and the radiation detector 3 are mounted at opposing positions on a rotatable gantry 7 which is driven by a motor 8. By means of the motor 8, the gantry 7 can be rotated such that the x-ray source 2 and the radiation detector 3 can be rotated around an object to be imaged positioned within the examination region 5, where the z-axis shown in FIG. 1 corresponds to the axis of rotation. At each angular measurement position, each detector element of the radiation detector 3 acquires one projection value (in case of energy-discriminating radiation detector 3, each detector element acquires one projection value per energy range at each position). This projection value is measured with respect to a projection line which corresponds to a ray path from the x-ray source 2 to the detector element, i.e. to a straight line from the x-ray source 2 to the detector element.

Within the examination region 5, the object is placed on a support (not shown in the figure). In case the object is a patient body, the support may be configured as a patient table. By moving the object and the gantry 7 relative to each other in the direction of the z-axis (i.e. perpendicular to the beam direction and parallel to the rotation axis of the gantry 7), different so-called slices of the object can be imaged, where each slice corresponds to one z-position and where measurements for multiple slices can be made simultaneously in case a two-dimensional detector array is used. For this purpose, the support (and, thus, the object) may be displaced back and forth within the examination region 5 in the direction of the z-axis by means of a further motor 9. However, it is also possible that the support is not moved, but that the gantry 7 can be displaced in the direction of the z-axis.

The x-ray source 2 and the motors 8 and 9 for rotating the gantry 7 and moving the object support relative to the gantry 7 are coupled to a control unit 10 controlling the operation of the CT apparatus 1. With respect to the x-ray source 2, the control unit 10 particularly controls timing and power for generating x-ray radiation. Moreover, the control unit 10 controls the motors 8 and 9 in order to move and position the object relative to the x-ray source 2 and the radiation detector 3 in accordance with a control plan provided in the control unit 10.

The radiation detector 3 is coupled to a reconstruction unit 11 which reconstructs images on the basis of the measurement data collected by the radiation detector 3. These measurement data correspond to projection values of the object, which are acquired with respect to associated projection lines, and images can be reconstructed from these projections in a way known to a person skilled in the art.

The control unit 10 and the reconstruction unit 11 may be configured as computer devices which comprise processor units to execute computer programs implementing the routines carried out by the control unit 10 and the reconstruction unit 11. In one embodiment, the control unit 10 and the reconstruction unit 11 are implemented in separate computer devices. However, it is likewise possible that the control unit 10 and the reconstruction unit 11 are included in a single computer device and implemented in several processor units or a single processor unit of the computer device.

The CT apparatus 1 is capable of performing a sparse CT scan of the object. This means that for each slice, the x-ray beam is only switched on at selected angular positions, which correspond to the sampling positions of this embodiment, whereas few selected positions as possible are used in order to reduce the radiation dose applied to the object.

Figure 2:
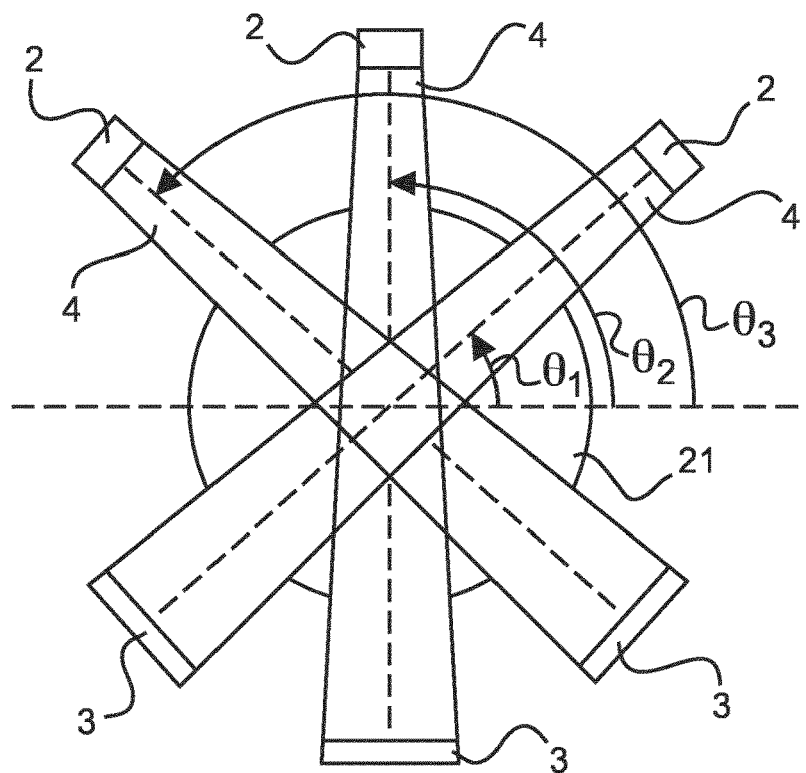

For carrying out the CT scan of a particular object, the selected angular positions for each slice may be defined in an object-specific control plan provided to the control unit 10. In case the object contour is approximately rotation-symmetric with respect to the z-axis for a slice, there may be a constant angular distance between neighboring sampling positions. This is schematically shown in FIG. 2 for a rotation-symmetric object 21 and three consecutive sampling positions $\theta_i$ (i=1, 2, 3). In case of on an asymmetric object contour, non-equiangular sampling positions are selected in order to achieve an approximately constant sampling density in the outer regions of the object (i.e. the regions having the largest distance to the z-axis).

The sampling positions are determined in a planning unit 12 of the CT apparatus 1, which generates the control plan that specifies the sampling positions. The planning unit 12 may likewise be configured as a software program executed on a computer device, which may correspond to the computer device implementing the control unit 10 and/or the reconstruction unit 11. The generation of the control plan in the planning unit 12 may be carried out during a planning phase prior to the execution of the actual sparse CT scan. Upon having generated the control plan, the planning unit 12 may transmit the control plan to the control unit 10, and the control unit 10 may control the execution of the sparse CT scan on the basis of the control plan.

In the planning unit 12, the sampling positions are determined—specifically for each relevant slice—on the basis of an estimate of the object contour, which may be determined in a way to be described further below. The determination is made on the basis of at least one ray path or projection line for each angular position. The projection line preferably corresponds to the central projection line of the radiation beam 4 and/or to the ray path through the z-axis, where it will be assumed in the following that the central projection line is used. In case the CT apparatus 1 provides a central field-of-view, the central projection line corresponds to ray path through the z-axis, i.e. the central projection line crosses the z-axis. However, in case the CT apparatus 1 provides an off-center field-of-view, the central projection line does not correspond to the ray path through the z-axis. In this case, the determination of the sampling position may also be made on the basis of the central projection line. Likewise it is possible to determine the sampling positions on the basis of the ray path through the z-axis.

Figure 3:
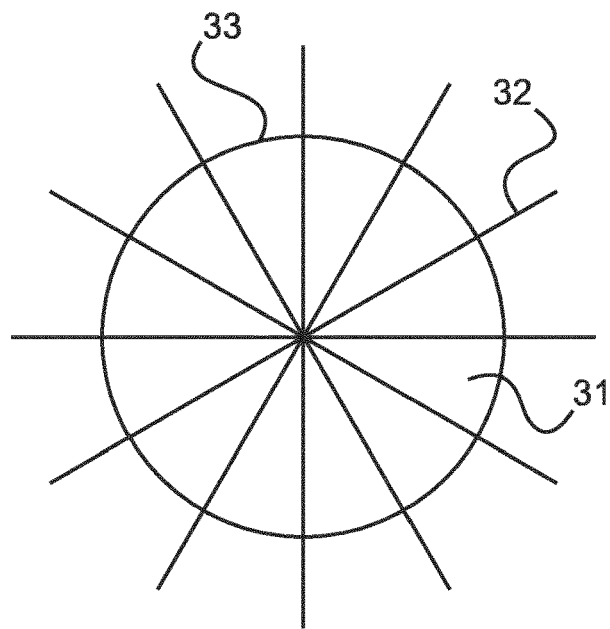

In the process of determining the sampling positions, it is the general aim to select the sampling positions in such a way that paths along the object contour between the object contour and the intersection points of the central projection lines of neighboring sampling positions approximately have the same length for all pairs of sampling positions. This is further illustrated in FIG. 3 schematically showing an asymmetric object 31 and the central projection lines of the sampling positions for a sparse CT scan, where one projection line is provided with the reference numeral 32. As shown in the figure the paths 33 along the object contour between the projection lines of neighboring sampling positions have an approximately equal length l (where only one path is provided with the reference numeral 33). The length l is selected in accordance with the desired sampling density, particularly in accordance with the desired sampling density in the object regions having a lower sampling density compared with other regions.

For this purpose, the planning unit 12 may estimate the contour of the object for each relevant z-position (i.e. the object contour in the x-y plane at the z-position), where each relevant z-position corresponds to one z-position at which the radiation detector 3 will be positioned in order to make measurements. In case measurements for plural slices are made concurrently as explained above, the object contour may be estimated for a selected one of the z-positions corresponding to the slices. Or, the object contour in the volume correspond to the plural slices may be estimated on the basis of the contour in each of the slices. For example, this may be done by calculating a mean or maximum radius for regular angular positions and by interpolating the contour between theses angular positions.

Upon determination of the object contour, the planning unit 12 may divide the contour into sections of equal length l (which sections correspond to the paths referred to above) and may determine the sample positions such that the central projection lines of the sample positions correspond to the end points of the sections. In such a way the sampling positions may be determined for each slice.

In further embodiments, the planning unit 12 effectively approximates the estimated object contour by means of straight paths, which may particularly connect the central projection lines of the sampling positions. These embodiments have the advantage that the computational complexity is reduced compared with the aforementioned embodiment in which the length of the contour of the object is determined for each slice.

In order to determine the sampling positions in these embodiments, the planning unit 12 may select the first sampling position using a certain predefined criterion. The first sampling position may correspond to an angular position of 0° or to another angular position. Starting from the first sampling position, the planning unit 12 may then determine the other sampling positions in such a way that the aforementioned aim is approximately achieved. In particular, the planning unit 12 may determine one sampling position on the basis of the preceding (in clockwise or anti-clockwise direction) neighboring sampling position.

For determining a sampling position on the basis of the preceding sampling position, one of several procedures may be applied. In some implementations, which are schematically illustrated in FIG. 4, the planning unit 12 determines a sampling position such that a straight path 41 between the central projection lines 42a, 42b of neighboring sampling positions (i.e. the sampling position to be determined and the preceding sampling position), which is substantially perpendicular to the bisecting line 43 has a predetermined length L, where the length L is equal for all such paths between central projection lines of neighboring sampling positions.

Figure 4:
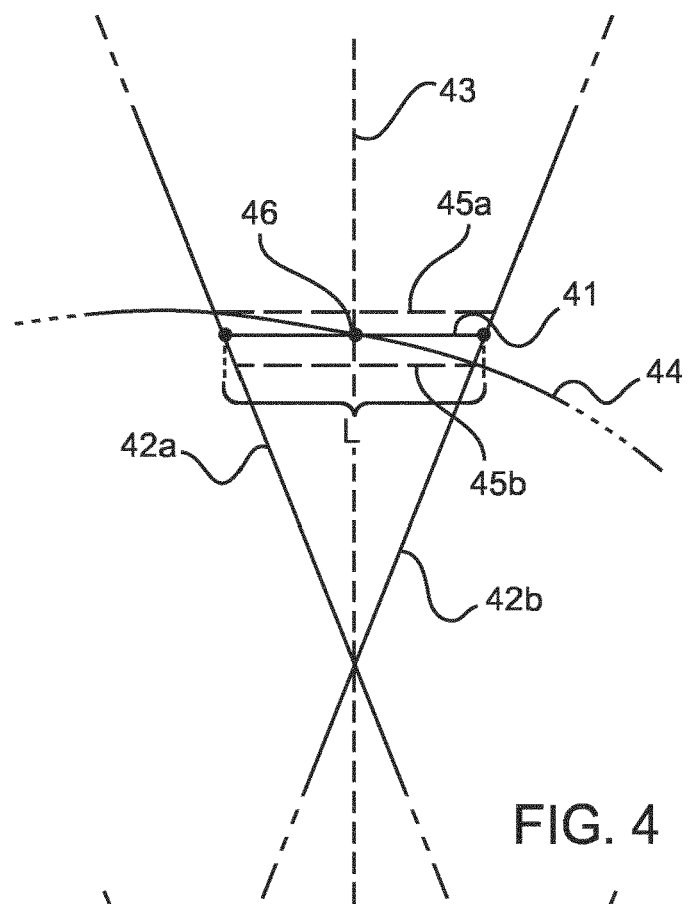

In one related implementation, the straight path 41 is selected such that it crosses the bisecting line 43 at the intersection point 46 between the bisecting line 43 and the object contour 44, as also illustrated in FIG. 4. In many cases, this implementation allows for a good approximation of the object contour by means of the straight paths 41. However, further implementations are likewise possible. So, the planning unit 12 may select the straight path 41 such that it crosses one of the central projection lines 42a,b of the sampling positions at the intersection point between the relevant central projection line 42a,b and the object contour 44. Such straight paths 45a, b are shown in FIG. 4 in dashed lines. Likewise, it is possible to select a straight path 41 which crosses the bisecting line between auxiliary lines corresponding to the straight paths 45a and 45b, i.e. auxiliary lines which are perpendicular to the bisecting line 43 and cross the central projection lines 42a,b of the sampling positions at the intersection points of the projection lines 42a,b and the object contour 44, respectively. In this regard, the planning unit 12 may particularly select the straight path crossing the bisecting line 43 at half the distance between the intersection points of the auxiliary lines 45a,b and the bisecting line 43.

Figure 5:
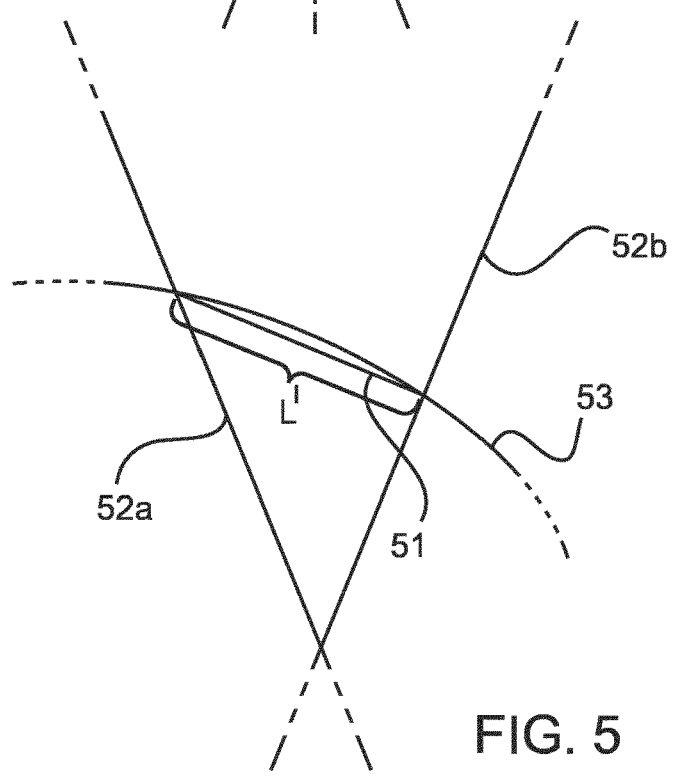

In accordance with an alternative procedure, which is schematically and exemplarily illustrated in FIG. 5, the planning unit 12 determines a sampling position for a slice such that a straight path 51 between the intersection point of the central projection line 52a of the sampling position and the object contour 53 and the intersection point of the central projection line 52b of a neighboring (e.g. subsequent) sampling position, has a predetermined length L', where the length L' is equal for all such paths between central projection lines of neighboring sampling positions. Thus, when iteratively determining the sampling positions for a slice, the planning unit 12 determines the intersection point of the central projection line of one sampling position (e.g. the projection line 52a) and the object contour 53. Then, the planning unit 12 determines the point of the contour 53 which can be connected to the determined intersection point by means of a straight path of length L'. The next sampling position corresponds to an angular position having a central projection line crossing the determined point of the contour 53.

The aforementioned procedure corresponds to the determination of a secant of the object contour 53, crossing the central projection lines 52a, 52b. As an alternative, it is also possible to determine a tangent of the object contour at a point of the object contour between the intersection points of the central projections lines and the object contour 53 and to determine the sampling positions such that the tangents at points between the central projection lines at the sampling positions have approximately equal lengths.

In accordance with one of the aforementioned procedures, the planning unit 12 may approximate the estimated object contour by means of straight paths, which may particularly connect the central projection lines of the sampling positions.

The object contour may be estimated before the actual sparse CT scan is executed using the control plan generated in the planning unit 12. For estimating the object contour, a CT scan with reduced radiation intensity may be made, i.e. a radiation intensity which is lower than the radiation intensity used in the actual sparse CT scan. Such a CT scan is also referred to as scout CT scan herein. During the scout CT scan, the object 41 is exposed to a significantly lower radiation dose than during a "full" CT scan. In particular, the scout CT scan may be a helical CT scan.

On the basis of the scout CT scan, a three-dimensional image of the object may be reconstructed in the reconstruction unit 11. This image may be provided to the planning unit 12, and the planning unit 12 may determine the object contour for each slice using the image. This may be done in an automatic process using image recognition techniques known to the person skilled in the art, for example, or in a semi-automatic process in which an operator controls the delineation of the object in order to determine the contour.

As an alternative, the object contour may also be determined on the basis of an earlier CT scan of the object made using the CT apparatus 1 or another CT apparatus. The measurement data of this earlier CT scan may be retrieved from a suitable storage means in which they have been stored upon the earlier CT scan and input into the planning unit 12, which determines the object contour using these measurement data.

As a further alternative, the object contour may be estimated on the basis of one or two two-dimensional images. One of these images may show the object in the y-z plane or horizontal plane (i.e. from above or below in case the object is a patient positioned on a patient table), and the other image may show the objet in the z-x-plane or vertical plane (i.e. from one side in case the object is a patient positioned on a patient table). These images show the transversal dimensions (in y-direction) and the sagittal dimensions (in x-direction) of the object for the relevant slices. From this information, the planning unit 12 may estimate to the contour of the object on the basis of a model of the object. This model may be based on general characteristics of the shape of the object, such as the general characteristics of the shape of the human body or the relevant part thereof. If only one of the images is captured, also the information of the other image may be estimated by the planning unit on the basis of an object model.

In one implementation, the two-dimensional image(s) is/are x-ray images which are acquired by means of the x-ray source 2 and the radiation detector 3 and which may be reconstructed in the reconstruction unit 11. In a further implementation, the two dimensional images are acquired in the visibly spectrum using a camera 13, which may optionally mounted at the gantry 7. Using one camera, the two images may be captured successively and the gantry 7 may be rotated between the capturing of the images. Alternatively, two cameras 13 may be provided at the gantry 7. The two-dimensional images produced in the reconstruction unit 11 or captured using the camera 13 may be provided to the planning unit 12, which may estimate the contour of the object on the basis of the images as explained above.

Likewise, the object contour may be estimated in another way. So, a three-dimensional optical scanner, such as a laser scanner, may be used for this purpose, which may be integrated into the CT apparatus 1, or which may be a separate device for scanning the object before it is positioned in the examination region 5 of the CT apparatus 1. In further embodiments, a determination of the actual dimensions of the object may be dispensed with. Rather, a number of predefined typical contours may be stored in the planning unit 12, and the planning unit may use the predefined contour, which best matches the object to be imaged. In this embodiment, the selection of the best matching predefined contour may be made by an operator of the CT apparatus, e.g. on the basis of some measurements of the object performed by the operator.

Using the embodiments described above, it is possible to determine angular sampling positions for a CT scan so that a sparse angular sampling technique can be applied with an optimized sampling density. In a similar way, sampling positions can be determined for a sparse angular sampling technique in other tomographic imaging techniques, such as MRI and SPECT. Also, the skilled person will appreciate that in a similar manner sampling positions for a sparse angular sampling can be determined in case the radiation detector 3 is not rotated around a fixed axis along a circular or spiral track but is moved along another curved track as it may be the case in C-arm CT imaging, for example.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single unit or device may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention claimed is:

1. A tomographic imaging device, comprising:
   a radiation source configured to emit radiation that travels through an object to be imaged;
   a radiation detector for measuring the radiation traveling through the object to be imaged, the radiation detector being configured to measure radiation traveling along at least one ray path only at a plurality of selected sampling positions on a curved track around an axis;
   a control unit comprising a processor configured to control the radiation source to emit radiation only when the radiation detector is positioned at the selected sampling positions; and
   a planning unit comprising the processor configured to determine the selected sampling positions by dividing an estimated contour of the object in a plane substantially perpendicular to the axis into sections of approximately equal length such that paths along the contour of the object between intersection points of the same at least one ray path at neighboring angular sampling positions and the contour of the object have approximately equal lengths.

2. The tomographic imaging device as defined in claim 1, the radiation source and the radiation detector being movable around the object.

3. The tomographic imaging device as defined in claim 2, wherein the radiation comprises x-ray radiation and wherein the radiation detector acquires projection values of the object.

4. The tomographic imaging device as defined in claim 2, further configured to perform a computed tomography scan to generate a three-dimensional image of the object on the basis of radiation registered by the radiation detector during the scan, wherein the processor is configured to estimate the contour of the object on the basis of the image.

5. The tomographic imaging device as defined in claim 4, wherein the at least one image is acquired in a visible spectrum and wherein the computed tomography device further comprises a camera for capturing the at least one image.

6. The tomographic imaging device as defined in claim 1, wherein the processor is configured to determine a bisecting line between the ray paths at neighboring selected sampling positions and to determine a straight connection path between said ray paths, which connection path crosses the bisecting line and is substantially perpendicular to the bisecting line, and wherein the processor is configured to determine the selected sampling positions in such a way that the connection paths for neighboring selected sampling positions have a substantially equal length.

7. The tomographic imaging device as defined in claim 6, wherein the connection path is selected such that it crosses an intersection point between the bisecting line and the contour of the object.

8. The tomographic imaging device as defined in claim 6, wherein the connection path is selected such that it crosses the bisecting line between a first and a second point, each of the first and second points corresponding to an intersection point between the bisecting line and a straight line which is substantially perpendicular to the bisecting line and crosses one of the ray paths at the intersection point between the ray path and the contour of the object.

9. The tomographic imaging device as defined in claim 1, wherein the processor is configured to determine the sampling positions in such a way that straight paths between intersection points of the ray paths at neighboring selected sampling positions and the contour of the object have an approximately equal length.

10. The tomographic imaging device as defined in claim 1, wherein the processor is configured to estimate the contour of the object on the basis of at least one two-dimensional image.

11. The tomographic imaging device as defined in claim 10, wherein the processor is configured to estimate the contour of the object on the basis of two two-dimensional images of the object captured along substantially perpendicular directions.

12. The tomographic imaging device as defined in claim 10, where the at least one two-dimensional image is generated using the radiation source and the radiation detector.

13. A method for operating a tomographic imaging device comprising a radiation source for emitting radiation that travels through an object to be imaged and a radiation detector for measuring radiation traveling along at least one ray path through the object to be imaged at sampling positions on a curved track around an axis, the method comprising:
   determining, with a processor, the selected sampling positions by dividing an estimated contour of the object in a plane substantially perpendicular to the axis into sections of approximately equal length such that paths along the contour of the object between intersection points of the same at least one ray path at neighboring angular sampling positions and the contour of the object have approximately equal lengths;
   controlling, with the processor, the radiation source to emit the radiation that travels through the object to be imaged only when the radiation detector is positioned at the selected sampling positions; and
   controlling, with the processor, the radiation detector such that the radiation detector measures radiation only at the selected sampling positions.

14. The method of claim 13, further comprising:
   moving the radiation source and the radiation detector around the object.

15. The method of claim 14, wherein the radiation comprises x-ray radiation, and further comprising controlling the radiation detector to acquire projection values of the object.

16. The method of claim 13, further comprising:
   determining, with the processor, a bisecting line between ray paths at neighboring selected sampling positions and a straight connection path between said ray paths, which connection path crosses the bisecting line and is substantially perpendicular to the bisecting line; and determining, with the processor, the selected sampling positions in such a way that the connection paths for neighboring selected sampling positions have a substantially equal length.

17. A non-transitory computer readable medium storing a computer program executable by a processor of a tomographic imaging device, the computer program comprising program code means for causing the processor to:
  determine selected sampling positions by dividing an estimated contour of an object in a plane substantially perpendicular to an axis into sections of approximately equal length such that paths along the contour of the object between intersection points of a same at least one ray path at neighboring angular sampling positions and the contour of the object have approximately equal lengths;
  control a radiation source to emit radiation that travels through the object to be imaged only when a radiation detector is positioned at the selected sampling positions; and
  control the radiation detector such that the radiation detector measures radiation only at the selected sampling positions.

18. The non-transitory computer readable medium of claim 17, wherein the computer program further causes the processor to:
  move the radiation source and the radiation detector around the object.

19. The non-transitory computer readable medium of claim 17, wherein the radiation comprises x-ray radiation, and the computer program further causes the processor to:
  control the radiation detector to acquire projection values of the object.

20. The non-transitory computer readable medium of claim 17, wherein the computer program further causes the processor to:
  determine a bisecting line between ray paths at neighboring selected sampling positions and a straight connection path between said ray paths, which connection path crosses the bisecting line and is substantially perpendicular to the bisecting line; and
  determine the selected sampling positions in such a way that the connection paths for neighboring selected sampling positions have a substantially equal length.

\* \* \* \* \*